United States Patent
Baez et al.

(12)

(10) Patent No.: US 6,242,251 B1
(45) Date of Patent: Jun. 5, 2001

(54) RHESUS NEUROPEPTIDE Y5 RECEPTOR

(75) Inventors: Melvyn Baez, Zionsville; Peiyi Yang, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/040,958

(22) Filed: Mar. 18, 1998

Related U.S. Application Data

(60) Provisional application No. 60/040,803, filed on Mar. 18, 1997.

(51) Int. Cl.[7] ............................. C12N 5/02; C12N 15/12
(52) U.S. Cl. ..................... 435/325; 536/23.1; 536/23.5; 435/69.1; 435/252.3; 435/252.33; 435/320.1
(58) Field of Search ..................... 530/350; 536/23.1, 536/25.5; 435/69.3, 252.3, 325, 7.1, 69.1, 252.33, 320.1

(56) References Cited

PUBLICATIONS

Gerald et al. A receptor subtype involved in neuropeptide–Y–0induced food intake. Nature, vol. 368, pp. 168–171 (1996).*

Golos et al. Cloning of four growth hormone/chorionic somatomammotropin–related complementary deoxyribonucleic acids differentially expressed during pregnancy in the Rhesus monkey placenta. Endocrinology, vol. 133, pp. 1744–1752, 1993.*

Kloster et al. Molecular cloning and characterization of the DNA of two papillomaviruses from monkeys. Virology, vol. 166, pp. 30–40, 1988.*

Stratagene 1991 Catalog, "Prime–it random primer labeling kit," Cat. # 300387, p. 66.*

Golos et al., Endocrinology 133: 1744–1752, 1993.*

Kloster et al., Virology 166: 30–40, 1988.*

Darnell et al., Molecular Cell Biology, pp. 107–108 and 255–258, 1986.*

Johnstone et al., Biochem. Biophys. Research Communications 220: 710–718, 1996.*

Boehringer Mannheim Biochemicals 1991 Catalog, p. 557.*

Geysen. Cognitive features of continous antigenic determinants. Journal of Molecular Recognition, vol. 1, pp. 32–41 (1988).*

\* cited by examiner

*Primary Examiner*—Marianne P. Allen
(74) *Attorney, Agent, or Firm*—Manisha A. Desai; Paul J. Gaylo

(57) ABSTRACT

This invention describes a novel rhesus receptor having affinity for neuropeptide Y, pancreatic polypeptide, and peptide YY. This invention also encompasses nucleic acids encoding this receptor, or a fragment thereof, as well as methods employing this receptor and the nucleic acid compounds.

15 Claims, No Drawings

RHESUS NEUROPEPTIDE Y5 RECEPTOR

This application claims the benefit of U.S. Provisional patent application Ser. No. 60/040,803 filed Mar. 18, 1997.

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced about ten years ago from porcine brain as part of a general screening protocol to discover carboxy-terminal amidated peptides and was named neuropeptide Y due to its isolation form neural tissue and the presence of tyrosine as both the amino and carboxy terminal amino acid. Neuropeptide Y is a member of the pancreatic family of peptides and shares significant sequence homology with pancreatic polypeptide, and peptide YY.

Neuropeptide Y and the other members of its family of peptides all feature a tertiary structure consisting of an N-terminal polyproline helix and an amphiphilic a-helix, connected with a b-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypothalamus, amygdala, and thalamus as well as being present in the peripheral nervous system in sympathetic neurons and adrenal chromaffin cells.

Neuropeptide Y seems to fulfill the main neurotransmitter criteria, since it is stored in synaptic granules, is released upon electrical nerve stimulation, and acts at specific receptors. It is dear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanine nucleotides, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and the closely related peptide YY. The Y1 receptor subtype appears to be the major vascular neuropeptide Y receptor. The Y2 receptor subtypes can also occur postjunctionally on vascular smooth muscle. The Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see. e.g. C. Wahlestedt and D. Reis, *Annual Review of Pharmacology and Toxicology* 33:309–352 (1993); NEUROPEPTIDE Y AND DRUG DEVELOPMENT (L. Grundemar and S. R. Bloom, eds., 1997, Academic Press].

In view of the wide number of clinical maladies associated with an excess of neuropeptide Y and related peptides, the development of neuropeptide Y receptor antagonists will serve to control these clinical conditions. The earliest such receptor antagonists were peptide derivatives. These antagonists proved to be of limited pharmaceutical utility because of their metabolic instability.

The present invention provides an additional receptor from the rhesus neuropeptide Y receptor family, the receptor of the present invention being designated the Y5 receptor, to those previously known. The characterization and treatment of physiological disorders is hereby furthered.

SUMMARY OF THE INVENTION

This invention provides an isolated amino acid compound useful as a receptor for neuropeptide Y and related peptides, said compound comprising the amino acid sequence

```
Met Asp Leu Glu Leu Asp Glu Tyr Tyr Asn Lys Thr Leu Ala Thr Glu
 1               5                  10                  15

Asn Asn Thr Ala Ala Thr Arg Asn Ser Asp Phe Pro Val Trp Asp Asp
            20                  25                  30

Tyr Lys Ser Ser Val Asp Asp Leu Gln Thr Phe Leu Ile Gly Leu Tyr
        35                  40                  45

Thr Phe Val Ser Leu Leu Gly Phe Met Gly Asn Leu Leu Ile Leu Met
    50                  55                  60

Ala Leu Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95
```

-continued

```
Phe Thr Leu Thr Ser Val Leu Leu Asp Gln Trp Met Phe Gly Lys Val
            100                 105                 110

Met Cys His Ile Met Pro Phe Leu Gln Cys Val Ser Val Leu Val Ser
            115                 120                 125

Thr Leu Ile Leu Ile Ser Ile Ala Ile Val Arg Tyr His Met Ile Lys
            130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
            180                 185                 190

Ser Ser Arg Tyr Leu Cys Val Glu Ser Trp Pro Ser Asp Ser Tyr Arg
            195                 200                 205

Ile Ala Phe Thr Ile Ser Leu Leu Val Gln Tyr Ile Leu Pro Leu
            210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Arg Lys Ile Gly Pro Gln Val Lys Leu Ser
            260                 265                 270

Gly Ser His Lys Trp Ser Tyr Ser Phe Ile Lys Lys His Arg Arg Arg
            275                 280                 285

Tyr Ser Lys Lys Thr Ala Cys Val Leu Pro Ala Pro Glu Arg Pro Ser
            290                 295                 300

Gln Glu Asn His Ser Arg Ile Leu Pro Glu Asn Phe Gly Ser Val Arg
305                 310                 315                 320

Ser Gln Leu Ser Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
            355                 360                 365

Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
            420                 425                 430

Lys Ala Asp Leu Met Ser Leu Ile His Cys Leu His Met
            435                 440                 445
                                                        55
``` hereinafter designated as SEQ ID NO:2.

The invention also provides an isolated nucleic acid compound that comprises a nucleic acid sequence which encodes the amino acid compounds provided. Particularly this invention provides the isolated nucleic acid compound having the sequence

```
GGATATCTGC AGAATTCAGG TGCTGACAAA TGTCTTTTTA TTCCAAGCAG GACTATAAT        59

ATG GAT TTA GAG CTC GAT GAA TAT TAT AAC AAG ACA CTT GCC ACA GAG   107
           Met Asp Leu Glu Leu Asp Glu Tyr Tyr Asn Lys Thr Leu Ala Thr Glu
            1               5                  10                  15
```

-continued

| | | | | | | | | | | | | | | | | |
|---|---|---|---|---|---|---|---|---|---|---|---|---|---|---|---|---|
| AAT | AAT | ACT | GCT | GCC | ACT | CGG | AAT | TCT | GAT | TTC | CCA | GTC | TGG | GAT | GAC | 155 |
| Asn | Asn | Thr | Ala | Ala | Thr | Arg | Asn | Ser | Asp | Phe | Pro | Val | Trp | Asp | Asp | |
| | | | 20 | | | | | 25 | | | | | 30 | | | |
| TAT | AAA | AGC | AGT | GTA | GAT | GAC | TTA | CAG | TAT | TTT | CTG | ATT | GGG | CTC | TAT | 203 |
| Tyr | Lys | Ser | Ser | Val | Asp | Asp | Leu | Gln | Tyr | Phe | Leu | Ile | Gly | Leu | Tyr | |
| | | 35 | | | | | 40 | | | | | 45 | | | | |
| ACA | TTT | GTA | AGT | CTT | CTT | GGC | TTT | ATG | GGG | AAT | TTA | CTT | ATT | TTA | ATG | 251 |
| Thr | Phe | Val | Ser | Leu | Leu | Gly | Phe | Met | Gly | Asn | Leu | Leu | Ile | Leu | Met | |
| | 50 | | | | | 55 | | | | | 60 | | | | | |
| GCT | CTC | ATG | AAA | AAG | CGT | AAT | CAG | AAG | ACT | ACG | GTA | AAC | TTC | CTT | ATA | 299 |
| Ala | Leu | Met | Lys | Lys | Arg | Asn | Gln | Lys | Thr | Thr | Val | Asn | Phe | Leu | Ile | |
| 65 | | | | | 70 | | | | | 75 | | | | | 80 | |
| GGA | AAT | CTG | GCC | TTT | TCT | GAT | ATC | TTG | GTT | GTG | CTG | TTT | TGC | TCA | CCT | 347 |
| Gly | Asn | Leu | Ala | Phe | Ser | Asp | Ile | Leu | Val | Val | Leu | Phe | Cys | Ser | Pro | |
| | | | | 85 | | | | | 90 | | | | | 95 | | |
| TTC | ACA | CTG | ACA | TCT | GTC | TTG | CTG | GAT | CAG | TGG | ATG | TTT | GGC | AAA | GTC | 395 |
| Phe | Thr | Leu | Thr | Ser | Val | Leu | Leu | Asp | Gln | Trp | Met | Phe | Gly | Lys | Val | |
| | | | 100 | | | | | 105 | | | | | 110 | | | |
| ATG | TGC | CAT | ATT | ATG | CCT | TTT | CTG | CAA | TGC | GTG | TCA | GTT | TTG | GTT | TCA | 443 |
| Met | Cys | His | Ile | Met | Pro | Phe | Leu | Gln | Cys | Val | Ser | Val | Leu | Val | Ser | |
| | | 115 | | | | | 120 | | | | | 125 | | | | |
| ACT | TTA | ATT | TTA | ATA | TCA | ATT | GCC | ATT | GTC | AGG | TAT | CAT | ATG | ATA | AAA | 491 |
| Thr | Leu | Ile | Leu | Ile | Ser | Ile | Ala | Ile | Val | Arg | Tyr | His | Met | Ile | Lys | |
| | 130 | | | | | 135 | | | | | 140 | | | | | |
| CAT | CCC | ATC | TCT | AAT | AAT | TTA | ACA | GCA | AAC | CAT | GGC | TAC | TTT | CTG | ATA | 539 |
| His | Pro | Ile | Ser | Asn | Asn | Leu | Thr | Ala | Asn | His | Gly | Tyr | Phe | Leu | Ile | |
| 145 | | | | | 150 | | | | | 155 | | | | | 160 | |
| GCT | ACT | GTC | TGG | ACA | CTA | GGT | TTT | GCC | ATC | TGT | TCT | CCC | CTT | CCA | GTG | 587 |
| Ala | Thr | Val | Trp | Thr | Leu | Gly | Phe | Ala | Ile | Cys | Ser | Pro | Leu | Pro | Val | |
| | | | | 165 | | | | | 170 | | | | | 175 | | |
| TTT | CAC | AGT | CTT | GTG | GAA | CTT | CAA | GAA | ACA | TTT | GGT | TCA | GCG | TTG | CTG | 635 |
| Phe | His | Ser | Leu | Val | Glu | Leu | Gln | Glu | Thr | Phe | Gly | Ser | Ala | Leu | Leu | |
| | | | 180 | | | | | 185 | | | | | 190 | | | |
| AGC | AGC | AGG | TAT | TTA | TGT | GTT | GAG | TCA | TGG | CCA | TCT | GAT | TCA | TAC | AGA | 683 |
| Ser | Ser | Arg | Tyr | Leu | Cys | Val | Glu | Ser | Trp | Pro | Ser | Asp | Ser | Tyr | Arg | |
| | | 195 | | | | | 200 | | | | | 205 | | | | |
| ATT | CCC | TTT | ACT | ATC | TCT | TTA | TTG | CTA | GTT | CAC | TAT | ATT | CTG | CCC | TTA | 731 |
| Ile | Ala | Phe | Thr | Ile | Ser | Leu | Leu | Val | Gln | Tyr | Ile | Leu | Pro | Leu | |
| | 210 | | | | | 215 | | | | | 220 | | | | | |
| GTT | TGT | CTT | ACT | GTA | AGT | CAT | ACA | AGT | GTC | TGC | AGA | AGC | ATA | AGC | TGT | 779 |
| Val | Cys | Leu | Thr | Val | Ser | His | Thr | Ser | Val | Cys | Arg | Ser | Ile | Ser | Cys | |
| 225 | | | | | 230 | | | | | 235 | | | | | 240 | |
| GGA | TTG | TCC | AAC | AAA | GAA | AAC | AGA | CTT | GAA | GAA | AAT | GAG | ATG | ATC | AAC | 827 |
| Gly | Leu | Ser | Asn | Lys | Glu | Asn | Arg | Leu | Glu | Glu | Asn | Glu | Met | Ile | Asn | |
| | | | | 245 | | | | | 250 | | | | | 255 | | |
| TTA | ACT | CTT | CAT | CCA | TCC | AGA | AAG | ATT | GGG | CCT | CAG | GTG | AAA | CTC | TCT | 875 |
| Leu | Thr | Leu | His | Pro | Ser | Arg | Lys | Ile | Gly | Pro | Gln | Val | Lys | Leu | Ser | |
| | | | 260 | | | | | 265 | | | | | 270 | | | |
| GGC | AGC | CAT | AAA | TGG | AGT | TAT | TCA | TTC | ATC | AAA | AAA | CAC | AGA | AGG | AGA | 923 |
| Gly | Ser | His | Lys | Trp | Ser | Tyr | Ser | Phe | Ile | Lys | Lys | His | Arg | Arg | Arg | |
| | | 275 | | | | | 280 | | | | | 285 | | | | |
| TAT | AGC | AAG | AAG | ACA | GCA | TGT | GTG | TTA | CCC | GCT | CCA | GAA | AGA | CCT | TCT | 971 |
| Tyr | Ser | Lys | Lys | Thr | Ala | Cys | Val | Leu | Pro | Ala | Pro | Glu | Arg | Pro | Ser | |
| | | | 290 | | | | | 295 | | | | | 300 | | | |
| CAA | GAG | AAC | CAC | TCC | AGA | ATA | CTT | CCA | GAA | AAC | TTT | GGC | TCT | GTA | AGA | 1019 |
| Gln | Glu | Asn | His | Ser | Arg | Ile | Leu | Pro | Glu | Asn | Phe | Gly | Ser | Val | Arg | |
| 305 | | | | | 310 | | | | | 315 | | | | | 320 | |
| AGT | CAG | CTC | TCT | TCA | TCC | AGT | AAG | TTC | ATA | CCA | GGG | GTC | CCC | ACT | TGC | 1067 |
| Ser | Gln | Leu | Ser | Ser | Ser | Ser | Lys | Phe | Ile | Pro | Gly | Val | Pro | Thr | Cys | |
| | | | | 325 | | | | | 330 | | | | | 335 | | |

-continued

```
TTT GAA ATA AAA CCT GAA GAA AAT TCA GAT GTT CAT GAA TTG AGA GTA      1115
Phe Glu Ile Lys Pro Glu Glu Asn Ser Asp Val His Glu Leu Arg Val
            340             345             350

AAA CGT TCT GTT ACA AGA ATA AAA AAG AGA TCT CGA AGT GTT TTC TAC      1163
Lys Arg Ser Val Thr Arg Ile Lys Lys Arg Ser Arg Ser Val Phe Tyr
        355             360             365

AGG CTG ACC ATA CTG ATA TTA GTA TTT GCT GTT AGT TGG ATG CCA CTA      1211
Arg Leu Thr Ile Leu Ile Leu Val Phe Ala Val Ser Trp Met Pro Leu
    370             375             380

CAC CTT TTC CAT GTG GTA ACT GAT TTT AAT GAC AAT CTT ATT TCA AAT      1259
His Leu Phe His Val Val Thr Asp Phe Asn Asp Asn Leu Ile Ser Asn
385             390             395             400

AGG CAT TTC AAG TTG GTG TAT TGC ATT TGT CAT TTG TTG GGC ATG ATG      1307
Arg His Phe Lys Leu Val Tyr Cys Ile Cys His Leu Leu Gly Met Met
            405             410             415

TCC TGT TGT CTT AAT CCA ATT CTG TAT GGA TTT CTT AAT AAT GGG ATT      1355
Ser Cys Cys Leu Asn Pro Ile Leu Tyr Gly Phe Leu Asn Asn Gly Ile
            420             425             430

AAA GCT GAT TTA ATG TCC CTT ATA CAC TGT CTT CAT ATG TAATAATTCT       1404
Lys Ala Asp Leu Met Ser Leu Ile His Cys Leu His Met
        435             440             445

CACCTGAATT CCAGCACACT GG                                             1426
``` which is hereinafter designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and adverse reaction profile of agents useful in the treatment or prevention of disorders associated with an excess or deficiency in the amount of neuropeptide Y present.

DETAILED DESCRIPTION AND PREFERRED EMBODIMENTS

The terms and abbreviations used in this document have their normal meanings unless otherwise designated. For example "_C" refers to degrees Celsius; "N" refers to normal or normality; "mmol" refers to millimole or millimoles; "g" refers to gram or grams; "ml" means milliliter or milliliters; "M" refers to molar or molarity, "µg" refers to microgram or micrograms; and "µl" refers to microliter or microliters.

All nucleic acid sequences, unless otherwise designated, are written in the direction from the 5' end to the 3' end, frequently referred to "5' as 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments. Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., MOLECULAR CLONING: A LABORATORY MANUAL, (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other neuropeptide Y receptor subtypes. This term may also be employed in the sense that such antibodies may be used to differentiate between the rhesus Y5 receptor protein and analogous proteins derived from other species.

The term "PCR" as used herein refers to the widely-known polymerase chain reaction employing a thermally-stable polymerase.

This invention provides the protein of SEQ ID NO:2, a rhesus neuropeptide Y receptor, designated as a Y5 receptor. [For a review of neuropeptide Y receptors, see, D. Gehlert, Life Sciences, 55:551–562 (1994)]. Traditional receptors of this family have considerable overlap in their binding affinities for neuropeptide Y and peptide YY while pancreatic polypeptide appears to have its own distinct set of receptors. Many, but not all, of the effects of neuropeptide Y can be replicated using peptide YY. The receptor of the present invention, as described infra, has considerable pharmacological overlap between pancreatic polypeptide and peptide YY and less affinity for neuropeptide Y, indicating it belongs to a novel subclass of receptors.

Two subtypes of receptors for neuropeptide Y were initially proposed on the basis of the affinity of the 13-36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13-36 fragment, but interacts with the full length neuropeptide Y and peptide YY with equal affinity. C. Wahlestedt, et al.. *Regulatory Peptides,* 13:307–318 (1986); C. Wahlestedt, et al., NEURONAL MESSENGERS IN VASCULAR FUNCTION, 231–241 (Nobin, et al., eds. 1987). Substitution of the amino acid at position 34 with a proline ($Pro^{34}$) results in a protein which is specific for the Y-1 receptor. E. K Potter, et al., *European Journal of Pharmacology* 193:15–19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC. [For a review, see, B. J. McDermott, et al., *Cardiovascular Research,* 27:893–905 (1993)]. This action is prevented by application of pertussis toxin confirming the role of a G protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., *Proceedings of the National Academy of Sciences (USA),* 89:5794–5798 (1992). The Y-1 receptor has been reported to couple to either second messenger system when studied using tissue preparations or cell lines naturally expressing the receptor. D. Gehlert, supra, at 553. The Y-1 receptor cannot, therefore, be distinguished solely on the basis of coupling to a single second messenger.

Modulation of a Y-1 receptor (either a typical or an atypical Y-1 receptor) is believed to influence multiple physiological conditions, including, but not limited to, obesity or appetite disorder, adult onset diabetes, bulimia nervosa, pheochromocytoma-induced hypertension, subarachnoid hemorrhage, neurogenic vascular hypertrophy, hypertension, anxiety, and anorexia nervosa. PCT Patent Publication WO 96/16542, published Jun. 6, 1996, at page 135, and the references cited therein.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13-36), though the 3-36 fragment of neuropeptide Y and peptide YY provides improved affinity and selectivity. Y. Dumont, et al., *Society for Neuroscience Abstracts,* 19:726 (1993). Like Y-1 receptor, this receptor is coupled to the inhibition of adenylate cyclase, though in some preparations it may not be sensitive to pertussis toxin. The Y-2 receptor was found to reduce the intracellular levels of calcium in the synapse by selective inhibition of N-type calcium channels. Like the Y-1 receptor, the Y-2 receptor may exhibit differential coupling to second messengers. The Y2 receptor is believed to be involved in modulating hypertension, epileptic seizure, and neurogenic vascular hypertrophy. PCT Patent Publication WO 96/16542, published Jun. 6, 1996, at page 135, and the references cited therein.

The Y-2 receptors are found in a variety of brain regions, including the hippocampus, substantia nigra-lateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters.

Y-3 Receptor

This receptor is the newest and least studied of the established neuropeptide Y receptor subtypes. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology,* 182:207–208 (1990). This receptor is believed to modulate hypertension. PCT Patent Publication WO 96/16542, published Jun. 6, 1996, at page 135, and the references cited therein.

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences,* 50:PL7–PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al. *Endocrinology,* 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to the crypt cells where intestinal chloride secretion is believed to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al., *Brain Research,* 604:304–317 (1993). While the pharmacology of this response resembled the Y-1 receptor, the 2-36 fragment of neuropeptide Y was significantly more potent than neuropeptide Y. In addition, intracerebroventricular neuropeptide Y(2-36) fully stimulates feeding, but does not reduce body temperature as does full length neuropeptide Y. F. B. Jolicoeur, et al. *Brain Research Bulletin,* 26:309–311 (1991). Two recent patent publications describe the cloning and expression of the Y5 receptor, believed to be the "feeding receptor". Patent Cooperation Treaty Publication WO 96116542, published Jun. 6, 1996; and Australian Patent Publication AU 956467 A0, published Nov. 30, 1995.

The receptors of the present invention are believed to potentiate central nervous system responses and is, therefore, an important target for pharmaceutical purposes. The receptor of the present invention will be useful in identifying compounds useful in the treatment or prevention of conditions associated with an excess of neuropeptide Y.

The term "physiological disorder associated with an inappropriate amount of neuropeptide Y, peptide YY, or pancreatic polypeptide" encompasses those disorders associated with an inappropriate stimulation of a receptor of these neuropeptides, regardless of the actual amount of the neuropeptide present in the locale.

These physiological disorders include:

- disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;
- conditions related to increased sympathetic nerve activity for example, during or after coronary artery surgery, and operations and surgery in the gastrointestinal tract;
- cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, and dementia;
- conditions related to pain or nociception;
- diseases related to abnormal gastrointestinal motility and secretion, such as different forms of ileus, urinary incontinence, and Crohn's disease;
- abnormal drink and food intake disorders, such as obesity, anorexia, bulimia, and metabolic disorders;
- diseases related to sexual dysfunction and reproductive disorders;
- conditions or disorders associated with inflammation;
- respiratory diseases, such as asthma and conditions related to asthma and bronchoconstriction; and
- diseases related to abnormal hormone release, such as leuteinizing hormone, growth hormone, insulin, and prolactin.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See. e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cydohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also J. Sambrook, et al. supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F−(j80dlacZDM15), D(lacZYA-argF)U169 supE44, 1−, hsdR17($r_K^-$, $m_K^+$), recA1, endA1, gyrA96, thi-1, relA1 |
| HB101 | supE44, hsdS20($r_B^- m_B^-$), recA13, ara-14, proA2 lacY1, galK2, rpsL20, xyl-5, mtl-1, mcrB, mrr |
| JM109 | recA1, e14−(mcrA), supE44, endA1, hsdR17($r_K^-$, $m_K^+$), gyrA96, relA1, thi-1, Æ(lac-proAB), F'[traD36, proAB+lacIq,lacZÆM15] |
| RR1 | supE44, hsdS20($r_B^- m_B^-$), ara-14 proA2, lacY1, galK2, rpsL20, xyl-5, mtl-5 |

-continued

| Strain | Genotype |
|---|---|
| c1776 | F⁻, ton, A53, dapD8, minA1, supE42 (glnV42), D(gal-uvrB)40, minB2, rfb-2, gyrA25, thyA142, oms-2, metC65, oms-1, D(bioH-asd)29, cycB2, cycA1, hsdR2, 1⁻ |
| 294 | endA, thi⁻, hsr⁻, hsm$_k$⁺(U.S. Pat. No. 4,366,246) |
| LE392 | F⁻, hsdR514(r⁻m⁻), supE44, supF58, lacY1, or Dlac(I-Y)6, galK2, glaT22, metB1, trpR55, 1⁻ |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of E. coli employed in the cloning and expression of the genes of this invention is RV308, which is available from the ATCC under accession number ATCC 31608, and is described in U.S. Pat. No. 4,551,433, issued Nov. 5, 1985.

In addition to the strains of E. coli discussed supra bacilli such as Bacillus subtilis, other enterobacteriaceae such as Salmonella typhimurium or Serratia marcescans and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the b-lactamase [vector pGX2907 (ATCC 39344) contains the replicon and β-lactamase gene] and lactose promoter systems [Chang et al., Nature (London), 275:615 (1978); and Goeddel et al., Nature (London). 281:544 (1979)], alkaline phosphatase, the tryptophan (trp) promoter system [vector pATHI1 (ATCC 37695) is designed to facilitate expression of an open reading frame as a trpE faision protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the rhesus neuropeptide Y-like receptor-encoding nucleic acids of the present invention. Exemplary host cells suitable for use in the present invention are listed in Table I

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPM18226 | Human Myeloma | ATCC CCL 155 |
| H4IIEC3 | Rat Hepatoma | ATCC CCL 1600 |
| C1271 | Mouse Fibroblast | ATCC CCL 1616 |
| 293 | Human Embryonal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit- promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See. e.g J. Schimke, *Cell* 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*. 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature* (London). 282:39 (1979); J. Kingsman et al., *Gene* 7:141 (1979); S. Tschemper et al., *Gene,* 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090,57091)], hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 6,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjunction with the CYC1 promoter on plasmid YEpsec--hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |

TABLE II-continued

| Original Residue | Exemplary Substitutions |
| --- | --- |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the rhesus Y5 receptor molecule may be produced using synthetic methodology. This synthesis of nucleic acids is well known in the art. See e.g., E. L. Brown, R. Belagaje, M. J. Ryan, and H. G. Khorana, *Methods in Enzymology,* 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See. e.g., M. J. Gait, ed., OLIGONUCLEOTIDE SYNTHESIS, A PRACTICAL APPROACH, (1984).

The synthetic rhesus Y5 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the Y5 receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO: 1, this invention also provides ribonucleic acids (RNA) which comprise the RNA sequence

```
CUCGAGCGGC CGCCAGUGUG AUGGAUAUCU GCAGAAUUCG GCUUAGGACU AUAAUAUGGA      60

UUUAGAGCUC GAUGAAUAUU AUAACAAGAC ACUUGCCACA GAGAAUAAUA CUGCUGCCAC     120

UCGGAAUUCU GAUUUCCCAG UCUGGGAUGA CUAUAAAAGC AGUGUAGAUG ACUUACAGUA     180

UUUUCUGAUU GGGCUCUAUA CAUUUGUAAG UCUUCUUGGC UUUAUGGGGA AUUUACUUAU     240

UUUAAUGGCU CUCAUGAAAA AGCGUAAUCA GAAGACUACU GUAAACUUCC UUAUAGGAAA     300

UCUGGCCUUU UCUGAUAUCU UGGUUGUGCU GUUUUGCUCA CCUUUCACAC UGACAUCUGU     360

CUUGCUGGAU CAGUGGAUGU UUGGCAAAGU CAUGUGCCAU AUUAUGCCUU UUCUGCAAUG     420

CGUGUCAGUU UUGGUUUCAA CUUUAAUUUU AAUAUCAAUU GCCAUUGUCA GGUAUCAUAU     480

GAUAAAACAU CCCAUCUCUA AUAAUUUAAC AGCAAACCAU GGCUACUUUC UGAUAGCUAC     540

UGUCUGGACA CUAGGUUUUG CCAUCUGUUC UCCCCUUCCA GUGUUUCACA GUCUUGUGGA     600

ACUUCAAGAA ACAUUUGGUU CAGCGUUGCU GAGCAGCAGG UAUUUAUGUG UUGAGUCAUG     660

GCCAUCUGAU UCAUACAGAA UUGCCUUUAC UAUCUCUUUA UUGCUAGUUC AGUAUAUUCU     720

GCCCUUAGUU UGUCUUACUG UAAGUCAUAC AAGUGUCUGC AGAAGCAUAA GCUGUGGAUU     780

GUCCAACAAA GAAAACAGAC UUGAAGAAAA UGAGAUGAUC AACUUAACUC UUCAUCCAUC     840

CAGAAAGAUU GGGCCUCAGG UGAAACUCUC UGGCAGCCAU AAAGGGAGUU AUUCAUUCAU     900

CAAAAAACAC AGAAGGAGAU AUAGCAAGAA GACAGCAUGU GUGUUACCCG CUCCAGAAAG     960

ACCUUCUCAA GAGAACCACU CCAGAAUACU UCCAGAAAAC UUUGGCUCUG UAAGAAGUCA    1020

GCUCUCUUCA UCCAGUAAGU UCAUACCAGG GGUCCCACU UGCUUUGAAA UAAAACCUGA    1080

AGAAAAUUCA GAUGUUCAUG AAUUGAGAGU AAAACGUUCU GUUACAAGAA UAAAAAAGAG    1140

AUCUCGAAGU GUUUUCUACA GGCUGACCAU ACUGAUAUUA GUAUUUGCUG UUAGUUGGAU    1200

GCCACUACAC CUUUUCCAUG UGGUAACUGA UUUUAAUGAC AAUCUUAUUU CAAAUAGGCA    1260

UUUCAAGUUG GUGUAUUGCA UUUGUCAUUU GUUGGGCAUG AUGUCCUGUU GUCUUAAUCC    1320

AAUUCUGUAU GGAUUUCUUA AUAAUGGGAU UAAAGCUGAU UUAAUGUCCC UUUAUACACUG   1380

UCUUCAUAUG UAAUAAUUCU CAGACUAGUC AAGCCGAAUU CCAGCACACU GGCGGCCGUU   1440

AC                                                                  1442
``` hereinafter referred to as SEQ ID NO:5, or the complementary ribonucleic acid, or a fragment of either SEQ ID NO:5 or the complement thereof. The ribonucleic acids of the present invention may be prepared using the polynucleotide synthetic methods discussed supra or they may be prepared enzymatically using RNA polymerases to transcribe a DNA template. complement thereof.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to rhesus genomic DNA or messenger RNA encoding a rhesus neuropeptide Y receptor, is provided. Preferably, the 18 or more base pair compound is DNA.

The term "selectively hybridize" as used herein may refer to either of two situations. In the first such embodiment of this invention, the nucleic acid compounds described supra hybridize to a rhesus neuropeptide Y receptor under more stringent hybridization conditions than these same nucleic acid compounds would hybridize to an analogous neuropeptide Y receptor of another species, e.g. murine or primate. In the second such embodiment of this invention, these probes hybridize to the Y5 receptor under more stringent hybridization conditions than other related compounds, including nucleic acid sequences encoding other neuropeptide Y receptors.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1.

Generation of a rhesus Y1-like clone by PCR

Two degenerate primers containing an appropriate cloning site are used on rhesus genomic DNA using the following PCR conditions: 5 min at 99° C. for one cycle, then 1 minute at 94° C., minute 2 at 42° C. and 3 minutes at 72° C. for 25 cycles using Taq polymerase. The PCR product is run on an agarose gel and a band corresponding to the appropriate size is cut out, added to 500 ml of water, boiled for 5 min and reamplified for 1 min at 94° C., 2 min at 42° C. and 2 min at 72° C. for 25 cycles. Three microliters of the generated product are ligated to 25 ng of a T vector (Novagen) using T4 DNA ligase and transformed into DH5a cells.

DNA sequencing

Sequence determinations are performed with dideoxy chain termination with an automated flourescent dye DNA sequencer (Applied Biosystems) or manually using [a-$^{35}$S] dATP followed by autoradiography. For manual sequencing either a T7 primer or a M13F (forward) primer is used.

Generation of a PCR probe for screening of library

A PCR product is generated with the rhesus clone as a template and using the same primers as previously under the following conditions: 1 minute at 94° C., 1 minute at 55° C. and 2 minutes at 72° C. for 25 cycles. The product is labeled with [a-$^{32}$P]dCTP using a random priming method. The probe is purified on a SEPHADEX G-50™ column to remove non-incorporated nucleotides.

Screening of a rhesus genomic library

A rhesus genomic DNA library made from lymphocytes in a commercially available lambda vector, lambda DASH™, is plated out with *E. coli* LE 392 as bacterial host strain. Hybridizations are carried out for 16 hours with high stringency at 65° C. in 25% formamide, 6×SSC, 10% Dextran sulfate, 5×Denhardt's solution and 0.1% SDS. Plaques are lifted with nylon membranes. Filters are washed twice at room temperature in 2×SSC, 0.5% SDS and twice for 30 minutes at 65° C. in 0.2×SSC, 0.5% SDS. The filters were exposed on film Screenings are carried out in three consecutive steps and single plaques are picked in the tertiary screening. A number of strongly hybridizing plaques are selected and a high titer stock is made for amplification of the phages.

Phage clone characterization

Phages are grown in *E. coli* LE 392 in liquid culture. Phage particles are collected and DNA is extracted and digested with various restriction enzymes and run on agarose gel. The gel is denatured and blotted onto a nylon membrane. The membrane is hybridized as described above with the rhesus probe and exposed on film. Hybridizing fragments are identified and cloned into the commonly used plasmid vector Bluescript KS+®. Plasmid DNA is prepared using commercially available kits. A restriction map is constructed for overlapping hybridizing clones.

Sequencing of the rhesus Y5 clone

Sequencing may be carried out as previously described using primers for manual or automated sequencing. Several different clones are typically sequenced.

Cloning into expression vector

If no suitable restriction sites are available in the receptor clone for cloning into the expression vector, two oligonucleotides may be used as primers to generate with PCR a fragment containing the entire coding region.

The PCR is run with VENT DNA POLYMERASE™ (a commercially available DNA polymerase cloned from the archaebacterium *Thermococcus litoralis,* New England Biolabs, Beverly, Mass.) and the rhesus Y1-like receptor clone as a template under the following conditions: 1 minute at 94° C., 1 minute at 50° C. and 2 minutes at 72° C. for 25 cycles. An aliquot of the PCR reaction is run on an agarose gel and displays the expected product of 1.25 kb. The remainder of the reaction is phenol extracted, cut with the appropriate restriction enzymes and run on a preparative agarose gel and collected onto a DEAE membrane. The DNA is eluted from the membrane and purified by phenol extraction. The fragment is then ligated into the expression vector.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The desired plasmid may be isolated from *E. coli* containing these plasmids using standard procedures such as cesium chloride DNA isolation.

Any plasmid comprising the gene of the present invention is readily modified to construct expression vectors that produce Y5 receptors in a variety of organisms, including, for example, *E. coli* Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, CURRENT PROTOCOLS IN MOLECULAR BIOLOGY, 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oligonucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is E. coli. An especially preferred expression vector in *E. coli* is one which comprises SEQ ID NO:1. Transformed host cells may be cultured under conditions well known to skilled artisans such that SEQ ID NO:2 is expressed, thereby producing the Y5 receptor in the recombinant host cell.

The ability of neuropeptide Y, pancreatic polypeptide, and peptide YY, to bind to the Y5 receptor is essential in the development of a multitude of indications. In developing agents which act as antagonists or agonists of the Y5 receptor, it would be desirable, therefore, to determine those agents which bind the Y5 receptor. Generally, such an assay includes a method for determining whether a substance is a functional ligand of the Y5 receptor, said method comprising contacting a functional compound of the Y5 receptor with said substance, monitoring binding activity by physically detectable means, and identifying those substances which effect a chosen response. Preferably, the physically detectable means is competition with labeled neuropeptide Y (or pancreatic polypeptide, or peptide YY) or binding of ligand in an oocyte transient expression system.

The instant invention provides such a screening system useful for discovering agents which compete with neuropeptide Y for binding to the Y5 receptor, said screening system comprising the steps of:
  a) isolating a rhesus Y5 receptor;
  b) exposing said rhesus Y5 receptor to a potential inhibitor or surrogate of the neuropeptide Y/Y5 receptor complex;
  c) introducing neuropeptide Y (or pancreatic polypeptide or peptide YY);
  d) removing non-specifically bound molecules; and
  e) quantifying the concentration of bound potential inhibitor and/or neuropeptide Y (or pancreatic polypeptide or peptide YY).

This allows one to rapidly screen for inhibitors or surrogates of the formation of the neuropeptide Y/Y5 receptor complex. Utilization of the screening system described above provides a sensitive and rapid means to determine compounds which interfere with the formation of the neuropeptide Y/Y5 receptor complex. This screening system may also be adapted to automated procedures such as a PANDEX® (Baxter-Dade Diagnostics) system allowing for efficient high-volume screening of potential therapeutic agents.

In the assay supra, as well those infra, the neuropeptide Y employed therein may be replaced with pancreatic polypeptide or peptide YY. The neuropeptide Y used as a ligand is, therefore, merely illustrative and is not to be considered limiting in any way.

In such a screening protocol a Y5 receptor is prepared as elsewhere described herein, preferably using recombinant DNA technology. A sample of a test compound is then introduced to the reaction vessel containing the Y5 receptor followed by the addition of neuropeptide Y (or pancreatic polypeptide or peptide YY). In the alternative the neuropeptide Y (or pancreatic polypeptide or peptide YY) may be added simultaneously with the test compound. Unbound molecules are washed free and the eluent inspected for the presence of neuropeptide Y (or pancreatic polypeptide or peptide YY) or the test compound.

For example, in a preferred method of the invention, radioactively or chemically labeled neuropeptide Y (or pancreatic polypeptide or peptide YY) may be used. The eluent is then scored for the chemical label or radioactivity. The absence or diminution of the chemical label or radioactivity indicates the formation of the neuropeptide Y/Y5 receptor complex. This indicates that the test compound has not effectively competed with neuropeptide Y in the formation of the neuropeptide Y/Y5 receptor complex. The presence of the chemical label or radioactivity indicates that the test compound has competed with neuropeptide Y in the formation of theneuropeptide Y/Y5 receptor complex. Similarly, a radioactively or chemically labeled test compound may be used in which case the same steps as outlined above would be used except that the interpretation of results would be the converse of using radioactively or chemically labeled neuropeptide Y.

As would be understood by the skilled artisan these assays may also be performed such that the practitioner measures the radioactivity or fluorescence remaining with the protein, not in the eluent. A preferred such assay employs radiolabeled neuropeptide Y (or pancreatic polypeptide or peptide YY). After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The Y5 receptor may be free in solution or bound to a solid support. Whether the Y5 receptor is bound to a support or is free in solution, it is generally important that the conformation of the protein be conserved. In a preferred practice of the invention, therefore, the Y5 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to Y5 receptor, because skilled artisans will recognize that any information regarding binding or selectivity of a particular compound is beneficial in the pharmaceutical development of drugs.

Assays useful for evaluating neuropeptide Y receptor antagonists are well known in the art See. e.g., U.S. Pat. No. 5,284,839, issued Feb. 8, 1994, which is herein incorporated by reference. See also, M. W. Walker, et al., *Journal of Neurosciences*, 8:2438–2446 (1988).

Transient transfection protocol

Cos-1 cells are seeded at a density of $10^5$ cells/150 mm dish on day one. On day three the cells are transfected (using commercially available kits) with either 25 μg rhesus Y5 receptor, 50 μg rhesus Y5 receptor, or 25 μg pSVLuc (SV40 Luciferase-control). Briefly, 4 ml media containing supercoiled DNA are combined with 4 ml media containing 0.6 ml of the commercial tranfection enhancing agent while mixing. This mixture is incubated for 15 minutes at room temperature, then 16 ml of media is added to the tube and gently mixed. The cells are washed with PBS and 10 ml is added per dish. The cells are incubated at 37° C. for 6 hours and 10 ml of media containing 20% fetal bovine serum is added. On day 5 (48 hrs post-transfection) the cells are scraped into phosphate buffered saline, pelleted, and kept on ice until binding assays are performed.

Stable transfection of CHO cells

The vector pTEJ-8, containing the Y5 receptor insert, is linearized using PvuI and transfected into Chinese hamster ovary (CHO) cells using commercially available reagents. The cells are maintained under 5% carbon dioxide in Dulbecco's Modified Eagle's Medium (DMEM)/Ham's F-12 Medium (3:1) containing 10% fetal bovine serum, 2 mM glutamine, 100 international units of penicillin, and 100 μg/ml streptomycin. Stably transfected cells are selected with 500 μg/ml G418 and tested for their ability to bind [$^{125}$I]-PYY, infra.

[125I]-PYY binding protocol

The homogenate binding studies are conducted using known methods. See e.g., D. R. Gehlert, et al., *Neurochemistry International*, 21: 45–67 (1992). The cell pellets are resuspended using a glass homogenizer in 25 mM HEPES (pH 7.4) buffer containing 2.5 mM calcium chloride, 1 mM magnesium chloride and 2 g/l Bacitracin. Incubations are performed in a final volume of 200 μl containing various concentrations [$^{125}$I]-pYy (SA 2200 Ci/mmol) or [$^{125}$I]-bPP (SA 2000 Ci/mmol) and 0.2–0.4 mg protein for 2 hours at room temperature. Nonspecific binding is defined as the amount of radioactivity remaining bound to the tissue after incubating in the presence of 1 μM hPP.

In pharmacological studies, various concentrations of peptides are included in the incubation mixture. Saturation experiments are performed with each radioligand by incubating in various concentrations of the radioligand in the assay. Incubations are terminated by rapid filtration through glass fiber filters, which had been presoaked in 0.3% polyethyleneimine, using a cell harvester. The filters are washed with 5 ml of 50 mM Tris (pH 7.4) at 4° C. and rapidly dried at 60° C. The dried filters are treated with melt-on scintillator sheets, and the radioactivity retained on the filters are counted. The results are analyzed using the Lundon-1 software package (Lundon Inc., Chagrin Falls, Ohio) running on a VAX computer or the Cheng-Prushoff equation. Protein concentrations are measured using standard staining techniques, using bovine serum albumin for standards.

In one such competition assay, a battery of known neuropeptide Y receptor antagonists, agonists, and partial agonists are evaluated for their relative abilities to inhibit the binding of [$^{125}$I]peptide YY to the rhesus Y5 receptor of the present invention.

The previously described screening systems identify compounds which competitively bind to the Y5 receptor. Determination of the ability of such compounds to stimulate or inhibit the action of the Y5 receptor is essential to further development of such compounds for therapeutic applications. The need for a bioactivity assay system which determines the response of the Y5 receptor to a compound is clear. The instant invention provides such a bioactivity assay, said assay comprising the steps of:

a) transfecting a mammalian host cell with an expression vector comprising DNA encoding a Y5 receptor;

b) culturing said host cell under conditions such that the DNA encoding the Y5 receptor is expressed, c) exposing said host cell so transfected to a test compound, and d) measuring the change in a physiological condition known to be influenced by the binding of neuropeptide Y to the Y5 receptor relative to a control in which the transfected host cell is exposed to neuropeptide Y.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of forskolin-stimulated cAMP synthesis is performed. The inhibition of cAMP synthesis is known to positively correlated with the addition of neuropeptide Y to cells containing certain types of neuropeptide Y receptors.

Adenylate Cyclase Activity

Adenylate cyclase activity is determined in initial experiments in transfected mammalian cells, using standard techniques. See, e.g., N. Adham, et al., supra.; R. L. Weinshank, et al., *Proceedings of the National Academy of Sciences (USA)*. 89:3630–3634 (1992), and the references cited therein.

Mammalian cells (the cell line AV12-664 is employed here) are stably transfected with a plasmid containing rhesus Y5 cDNA inserted in an appropriate plasmid vector (e.g., the pHD-derived plasmids). The cells are maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 μg/ml hygromycin.

For the assay the cells are disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, are added after the final wash. After incubating for 20 minutes at 37° C., 0.5 ml of 8 mM EDTA is added to each well. The plates are then placed in a boiling water bath for about four minutes. The supernatant fluids are then recovered from the wells and lyophilized. Cyclic adenosinemonophosphate determinations are carried out on the lyophilized samples using commercially available radioimmunoassay kits, following the manufacturer's instructions. The cAMP level in wells containing drug are then compared to the forskolin controls.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See. e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, HANDBOOK OF EXPERIMENTAL IMMUNOLOGY, (Blackwell Scientific Pub., 1986); J. Goding, MONOCLONAL ANTIBODIES: PRINCIPLES AND PRACTICE, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816, 567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., Science 242:423–426 (1988); PCT Publication No. WO 88/01649, which was published Mar. 10, 1988; U.S. Pat. No. 5,260,203, issued Nov. 9, 1993, the entire contents of which are herein incorporated by reference. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of Y5 receptors.

In addition to being functional as direct therapeutic and diagnostic aids, the availability of a family of antibodies which are specific for the Y5 receptor enables the development of numerous assay systems for detecting agents which bind to this receptor. One such assay system comprises radiolabeling Y5 receptor-specific antibodies with a radionuclide such as $^{125}I$ and measuring displacement of the radiolabeled Y5 receptor-specific antibody from solid phase Y5 receptor in the presence of a potential antagonist.

Numerous other assay systems are also readily adaptable to detect agents which bind Y5 receptor. Examples of these aforementioned assay systems are discussed in *Methods in*

*Enzymology,* (J. Langone. and H. Vunakis, eds. 1981), Vol. 73, Part B, the contents of which are herein incorporated by reference. Skilled artisans are directed to Section II of *Methods in Enzymology,* Vol. 73, Part B, supra, which discusses labeling of antibodies and antigens, and Section IV, which discusses immunoassay methods.

In addition to the aforementioned antibodies specific for the Y5 receptor, this invention also provides antibodies which are specific for the hypervariable regions of the anti-Y5 receptor antibodies. Some such anti-idiotypic antibodies would resemble the original epitope, the Y5 receptor, and, therefore, would be useful in evaluating the effectiveness of compounds which are potential antagonists, agonists, or partial agonists of the Y5 receptor. See e.g., Cleveland, et al., *Nature* (*London*) 305:56 (1983); Wasserman, et al. *Proceedings of the National Academy of Sciences* (*USA*), 79:4810 (1982).

What is claimed is:

1. An isolated polynucleotide compound encoding a receptor having affinity for Neuropeptide Y, Pancreatic Polypeptide, or Peptide YY, and comprising the amino acid sequence designated SEQ ID NO:2.

2. A composition comprising an isolated polynucleotide compound containing a sequence encoding the amino acid sequence of claim 1, wherein said sequence is selected from the group consisting of:

(a) SEQ ID NO:3;
(b) SEQ ID NO:5; and
(c) a polynucleotide compound fully complementary to (a) or (b).

3. A composition as claimed in claim 2 wherein the isolated polynucleotide compound is deoxyribonucleic acid.

4. A composition as claimed in claim 3 which is SEQ ID NO:3 or a sequence fully complementary to SEQ ID NO:3.

5. A composition as claimed in claim 4 comprising nucleotides 56 to 1390 of SEQ ID NO:3.

6. An expression vector capable of producing a functional rhesus Y5 receptor in a host cell which comprises a polynucleotide compound as claimed in claim 5 operably linked to regulatory elements necessary for expression of the polynucleotide compound in the host cell.

7. An expression vector as claimed in claim 6 for use in a host cell wherein the host cell is *Escherichia coli*.

8. An expression vector as claimed in claim 6 for use in a host cell wherein the host cell is a mammalian cell.

9. An expression vector as claimed in claim 8 which comprises the BK virus enhancer.

10. An expression vector as claimed in claim 9 which further comprises an adenovirus late promoter.

11. A transfected host cell comprising an expression vector as, claimed in claim 6.

12. A transfected host cell as claimed in claim 11 which is transfected *Escherichia coli*.

13. A transfected host cell as claimed in claim 11 which is a transfected mammalian cell.

14. A composition as claimed in claim 2 wherein the isolated polynucleotide compound is ribonucleic acid.

15. A composition as claimed in claim 14 which is SEQ ID NO:5.

* * * * *

```
                            SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
            (A) LENGTH: 1426 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 60..1394

(xi) SEQUENCE DESCRIPTION: SEQ ID NO: 1:

GGATATCTGC AGAATTCAGG TGCTGACAAA TGTCTTTTTA TTCCAAGCAG GACTATAAT         59

ATG GAT TTA GAG CTC GAT GAA TAT TAT AAC AAG ACA CTT GCC ACA GAG        107
    Met Asp Leu Glu Leu Asp Glu Tyr Tyr Asn Lys Thr Leu Ala Thr Glu
     1               5                  10                  15

AAT AAT ACT GCT GCC ACT CGG AAT TCT GAT TTC CCA GTC TGG GAT GAC        155
    Asn Asn Thr Ala Ala Thr Arg Asn Ser Asp Phe Pro Val Trp Asp Asp
                    20                  25                  30

TAT AAA AGC AGT GTA GAT GAC TTA CAG TAT TTT CTG ATT GGG CTC TAT        203
    Tyr Lys Ser Ser Val Asp Asp Leu Gln Tyr Phe Leu Ile Gly Leu Tyr
                35                  40                  45

ACA TTT GTA AGT CTT CTT GGC TTT ATG GGG AAT TTA CTT ATT TTA ATG        251
    Thr Phe Val Ser Leu Leu Gly Phe Met Gly Asn Leu Leu Ile Leu Met
            50                  55                  60

GCT CTC ATG AAA AAG CGT AAT CAG AAG ACT ACG GTA AAC TTC CTT ATA        299
    Ala Leu Met Lys Lys Arg Asn Gln Lys Thr Thr Val Asn Phe Leu Ile
    65                  70                  75                  80

GGA AAT CTG GCC TTT TCT GAT ATC TTG GTT GTG CTG TTT TGC TCA CCT        347
    Gly Asn Leu Ala Phe Ser Asp Ile Leu Val Val Leu Phe Cys Ser Pro
                    85                  90                  95

TTC ACA CTG ACA TCT GTC TTG CTG GAT CAG TGG ATG TTT GGC AAA GTC        395
    Phe Thr Leu Thr Ser Val Leu Leu Asp Gln Trp Met Phe Gly Lys Val
                   100                 105                 110

ATG TGC CAT ATT ATG CCT TTT CTG CAA TGC GTG TCA GTT TTG GTT TCA        443
    Met Cys His Ile Met Pro Phe Leu Gln Cys Val Ser Val Leu Val Ser
               115                 120                 125

ACT TTA ATT TTA ATA TCA ATT GCC ATT GTC AGG TAT CAT ATG ATA AAA        491
    Thr Leu Ile Leu Ile Ser Ile Ala Ile Val Arg Tyr His Met Ile Lys
           130                 135                 140

CAT CCC ATC TCT AAT AAT TTA ACA GCA AAC CAT GGC TAC TTT CTG ATA        539
    His Pro Ile Ser Asn Asn Leu Thr Ala Asn His Gly Tyr Phe Leu Ile
    145                 150                 155                 160

GCT ACT GTC TGG ACA CTA GGT TTT GCC ATC TGT TCT CCC CTT CCA GTG        587
```

```
Ala Thr Val Trp Thr Leu Gly Phe Ala Ile Cys Ser Pro Leu Pro Val
            165                 170                 175

TTT CAC AGT CTT GTG GAA CTT CAA GAA ACA TTT GGT TCA GCG TTG CTG        635
Phe His Ser Leu Val Glu Leu Gln Glu Thr Phe Gly Ser Ala Leu Leu
            180                 185                 190

AGC AGC AGG TAT TTA TGT GTT GAG TCA TGG CCA TCT GAT TCA TAC AGA        683
Ser Ser Arg Tyr Leu Cys Val Glu Ser Trp Pro Ser Asp Ser Tyr Arg
            195                 200                 205

ATT GCC TTT ACT ATC TCT TTA TTG CTA GTT CAG TAT ATT CTG CCC TTA        731
Ile Ala Phe Thr Ile Ser Leu Leu Leu Val Gln Tyr Ile Leu Pro Leu
            210                 215                 220

GTT TGT CTT ACT GTA AGT CAT ACA AGT GTC TGC AGA AGC ATA AGC TGT        779
Val Cys Leu Thr Val Ser His Thr Ser Val Cys Arg Ser Ile Ser Cys
225                 230                 235                 240

GGA TTG TCC AAC AAA GAA AAC AGA CTT GAA GAA AAT GAG ATG ATC AAC        827
Gly Leu Ser Asn Lys Glu Asn Arg Leu Glu Glu Asn Glu Met Ile Asn
                245                 250                 255

TTA ACT CTT CAT CCA TCC AGA AAG ATT GGG CCT CAG GTG AAA CTC TCT        875
Leu Thr Leu His Pro Ser Arg Lys Ile Gly Pro Gln Val Lys Leu Ser
            260                 265                 270

GGC AGC CAT AAA TGG AGT TAT TCA TTC ATC AAA AAA CAC AGA AGG AGA        923
Gly Ser His Lys Trp Ser Tyr Ser Phe Ile Lys Lys His Arg Arg Arg
            275                 280                 285

TAT AGC AAG AAG ACA GCA TGT GTG TTA CCC GCT CCA GAA AGA CCT TCT        971
Tyr Ser Lys Lys Thr Ala Cys Val Leu Pro Ala Pro Glu Arg Pro Ser
            290                 295                 300

CAA GAG AAC CAC TCC AGA ATA CTT CCA GAA AAC TTT GGC TCT GTA AGA       1019
Gln Glu Asn His Ser Arg Ile Leu Pro Glu Asn Phe Gly Ser Val Arg
305                 310                 315                 320

AGT CAG CTC TCT TCA TCC AGT AAG TTC ATA CCA GGG GTC CCC ACT TGC       1067
Ser Gln Leu Ser Ser Ser Ser Lys Phe Ile Pro Gly Val Pro Thr Cys
                325                 330                 335

TTT GAA ATA AAA CCT GAA GAA AAT TCA GAT GTT CAT GAA TTG AGA GTA       1115
Phe Glu Ile Lys Pro Glu Glu Asn Ser Asp Val His Glu Leu Arg Val
            340                 345                 350

AAA CGT TCT GTT ACA AGA ATA AAA AAG AGA TCT CGA AGT GTT TTC TAC       1163
Lys Arg Ser Val Thr Arg Ile Lys Lys Arg Ser Arg Ser Val Phe Tyr
            355                 360                 365

AGG CTG ACC ATA CTG ATA TTA GTA TTT GCT GTT AGT TGG ATG CCA CTA       1211
Arg Leu Thr Ile Leu Ile Leu Val Phe Ala Val Ser Trp Met Pro Leu
            370                 375                 380

CAC CTT TTC CAT GTG GTA ACT GAT TTT AAT GAC AAT CTT ATT TCA AAT       1259
His Leu Phe His Val Val Thr Asp Phe Asn Asp Asn Leu Ile Ser Asn
385                 390                 395                 400

AGG CAT TTC AAG TTG GTG TAT TGC ATT TGT CAT TTG TTG GGC ATG ATG       1307
Arg His Phe Lys Leu Val Tyr Cys Ile Cys His Leu Leu Gly Met Met
                405                 410                 415

TCC TGT TGT CTT AAT CCA ATT CTG TAT GGA TTT CTT AAT AAT GGG ATT       1355
Ser Cys Cys Leu Asn Pro Ile Leu Tyr Gly Phe Leu Asn Asn Gly Ile
            420                 425                 430

AAA GCT GAT TTA ATG TCC CTT ATA CAC TGT CTT CAT ATG TAATAATTCT       1404
Lys Ala Asp Leu Met Ser Leu Ile His Cys Leu His Met
            435                 440                 445

CACCTGAATT CCAGCACACT GG                                              1426

(2) INFORMATION FOR SEQ ID NO: 2:

(i) SEQUENCE CHARACTERISTICS:
        (A) LENGTH: 445 amino acids
        (B) TYPE: amino acid
```

(D) TOPOLOGY: linear (ii) MOLECULE TYPE: protein (xi) SEQUENCE DESCRIPTION: SEQ ID NO: 2:

```
Met Asp Leu Glu Leu Asp Glu Tyr Tyr Asn Lys Thr Leu Ala Thr Glu
 1               5                  10                  15
Asn Asn Thr Ala Ala Thr Arg Asn Ser Asp Phe Pro Val Trp Asp Asp
            20                  25                  30
Tyr Lys Ser Ser Val Asp Asp Leu Gln Tyr Phe Leu Ile Gly Leu Tyr
        35                  40                  45
Thr Phe Val Ser Leu Leu Gly Phe Met Gly Asn Leu Leu Ile Leu Met
    50                  55                  60
Ala Leu Met Lys Lys Arg Asn Gln Lys Thr Thr Val Asn Phe Leu Ile
 65                  70                  75                  80
Gly Asn Leu Ala Phe Ser Asp Ile Leu Val Val Leu Phe Cys Ser Pro
                85                  90                  95
Phe Thr Leu Thr Ser Val Leu Leu Asp Gln Trp Met Phe Gly Lys Val
            100                 105                 110
Met Cys His Ile Met Pro Phe Leu Gln Cys Val Ser Val Leu Val Ser
        115                 120                 125
Thr Leu Ile Leu Ile Ser Ile Ala Ile Val Arg Tyr His Met Ile Lys
    130                 135                 140
His Pro Ile Ser Asn Asn Leu Thr Ala Asn His Gly Tyr Phe Leu Ile
145                 150                 155                 160
Ala Thr Val Trp Thr Leu Gly Phe Ala Ile Cys Ser Pro Leu Pro Val
                165                 170                 175
Phe His Ser Leu Val Glu Leu Gln Glu Thr Phe Gly Ser Ala Leu Leu
            180                 185                 190
Ser Ser Arg Tyr Leu Cys Val Glu Ser Trp Pro Ser Asp Ser Tyr Arg
        195                 200                 205
Ile Ala Phe Thr Ile Ser Leu Leu Leu Val Gln Tyr Ile Leu Pro Leu
    210                 215                 220
Val Cys Leu Thr Val Ser His Thr Ser Val Cys Arg Ser Ile Ser Cys
225                 230                 235                 240
Gly Leu Ser Asn Lys Glu Asn Arg Leu Glu Glu Asn Glu Met Ile Asn
                245                 250                 255
Leu Thr Leu His Pro Ser Arg Lys Ile Gly Pro Gln Val Lys Leu Ser
            260                 265                 270
Gly Ser His Lys Trp Ser Tyr Ser Phe Ile Lys Lys His Arg Arg Arg
        275                 280                 285
Tyr Ser Lys Lys Thr Ala Cys Val Leu Pro Ala Pro Glu Arg Pro Ser
    290                 295                 300
Gln Glu Asn His Ser Arg Ile Leu Pro Glu Asn Phe Gly Ser Val Arg
305                 310                 315                 320
Ser Gln Leu Ser Ser Ser Lys Phe Ile Pro Gly Val Pro Thr Cys
                325                 330                 335
Phe Glu Ile Lys Pro Glu Glu Asn Ser Asp Val His Glu Leu Arg Val
            340                 345                 350
Lys Arg Ser Val Thr Arg Ile Lys Lys Arg Ser Arg Ser Val Phe Tyr
        355                 360                 365
Arg Leu Thr Ile Leu Ile Leu Val Phe Ala Val Ser Trp Met Pro Leu
    370                 375                 380
His Leu Phe His Val Val Thr Asp Phe Asn Asp Asn Leu Ile Ser Asn
```

| | | | | | | | | | | | | |
|---|---|---|---|---|---|---|---|---|---|---|---|---|
|385| | | | |390| | | | |395| | |400|
|Arg|His|Phe|Lys|Val|Tyr|Cys|Ile|Cys|His|Leu|Leu|Gly|Met Met|
| | | | |405| | | | |410| | | |415|

Ser Cys Cys Leu Asn Pro Ile Leu Tyr Gly Phe Leu Asn Asn Gly Ile
            420                 425                 430

Lys Ala Asp Leu Met Ser Leu Ile His Cys Leu His Met
            435                 440                 445

(2) INFORMATION FOR SEQ ID NO: 3:

(i) SEQUENCE CHARACTERISTICS:
        (A) LENGTH: 1442 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 56..1390

(xi) SEQUENCE DESCRIPTION: SEQ ID NO: 3:

```
CTCGAGCGGC CGCCAGTGTG ATGGATATCT GCAGAATTCG GCTTAGGACT ATAAT ATG         58
                                                              Met
                                                                1

GAT TTA GAG CTC GAT GAA TAT TAT AAC AAG ACA CTT GCC ACA GAG AAT         106
Asp Leu Glu Leu Asp Glu Tyr Tyr Asn Lys Thr Leu Ala Thr Glu Asn
          5                  10                  15

AAT ACT GCT GCC ACT CGG AAT TCT GAT TTC CCA GTC TGG GAT GAC TAT         154
Asn Thr Ala Ala Thr Arg Asn Ser Asp Phe Pro Val Trp Asp Asp Tyr
         20                  25                  30

AAA AGC AGT GTA GAT GAC TTA CAG TAT TTT CTG ATT GGG CTC TAT ACA         202
Lys Ser Ser Val Asp Asp Leu Gln Tyr Phe Leu Ile Gly Leu Tyr Thr
 35                  40                  45

TTT GTA AGT CTT CTT GGC TTT ATG GGG AAT TTA CTT ATT TTA ATG GCT         250
Phe Val Ser Leu Leu Gly Phe Met Gly Asn Leu Leu Ile Leu Met Ala
 50                  55                  60                  65

CTC ATG AAA AAG CGT AAT CAG AAG ACT ACG GTA AAC TTC CTT ATA GGA         298
Leu Met Lys Lys Arg Asn Gln Lys Thr Thr Val Asn Phe Leu Ile Gly
             70                  75                  80

AAT CTG GCC TTT TCT GAT ATC TTG GTT GTG CTG TTT TGC TCA CCT TTC         346
Asn Leu Ala Phe Ser Asp Ile Leu Val Val Leu Phe Cys Ser Pro Phe
             85                  90                  95

ACA CTG ACA TCT GTC TTG CTG GAT CAG TGG ATG TTT GGC AAA GTC ATG         394
Thr Leu Thr Ser Val Leu Leu Asp Gln Trp Met Phe Gly Lys Val Met
        100                 105                 110

TGC CAT ATT ATG CCT TTT CTG CAA TGC GTG TCA GTT TTG GTT TCA ACT         442
Cys His Ile Met Pro Phe Leu Gln Cys Val Ser Val Leu Val Ser Thr
        115                 120                 125

TTA ATT TTA ATA TCA ATT GCC ATT GTC AGG TAT CAT ATG ATA AAA CAT         490
Leu Ile Leu Ile Ser Ile Ala Ile Val Arg Tyr His Met Ile Lys His
130                 135                 140                 145

CCC ATC TCT AAT AAT TTA ACA GCA AAC CAT GGC TAC TTT CTG ATA GCT         538
Pro Ile Ser Asn Asn Leu Thr Ala Asn His Gly Tyr Phe Leu Ile Ala
                150                 155                 160

ACT GTC TGG ACA CTA GGT TTT GCC ATC TGT TCT CCC CTT CCA GTG TTT         586
Thr Val Trp Thr Leu Gly Phe Ala Ile Cys Ser Pro Leu Pro Val Phe
            165                 170                 175

CAC AGT CTT GTG GAA CTT CAA GAA ACA TTT GGT TCA GCG TTG CTG AGC         634
His Ser Leu Val Glu Leu Gln Glu Thr Phe Gly Ser Ala Leu Leu Ser
            180                 185                 190
```

```
AGC AGG TAT TTA TGT GTT GAG TCA TGG CCA TCT GAT TCA TAC AGA ATT      682
Ser Arg Tyr Leu Cys Val Glu Ser Trp Pro Ser Asp Ser Tyr Arg Ile
        195                 200                 205

GCC TTT ACT ATC TCT TTA TTG CTA GTT CAG TAT ATT CTG CCC TTA GTT      730
Ala Phe Thr Ile Ser Leu Leu Leu Val Gln Tyr Ile Leu Pro Leu Val
210             215                 220                 225

TGT CTT ACT GTA AGT CAT ACA AGT GTC TGC AGA AGC ATA AGC TGT GGA      778
Cys Leu Thr Val Ser His Thr Ser Val Cys Arg Ser Ile Ser Cys Gly
                230                 235                 240

TTG TCC AAC AAA GAA AAC AGA CTT GAA GAA AAT GAG ATG ATC AAC TTA      826
Leu Ser Asn Lys Glu Asn Arg Leu Glu Glu Asn Glu Met Ile Asn Leu
            245                 250                 255

ACT CTT CAT CCA TCC AGA AAG ATT GGG CCT CAG GTG AAA CTC TCT GGC      874
Thr Leu His Pro Ser Arg Lys Ile Gly Pro Gln Val Lys Leu Ser Gly
                260                 265                 270

AGC CAT AAA TGG AGT TAT TCA TTC ATC AAA AAA CAC AGA AGG AGA TAT      922
Ser His Lys Trp Ser Tyr Ser Phe Ile Lys Lys His Arg Arg Arg Tyr
        275                 280                 285

AGC AAG AAG ACA GCA TGT GTG TTA CCC GCT CCA GAA AGA CCT TCT CAA      970
Ser Lys Lys Thr Ala Cys Val Leu Pro Ala Pro Glu Arg Pro Ser Gln
290             295                 300                 305

GAG AAC CAC TCC AGA ATA CTT CCA GAA AAC TTT GGC TCT GTA AGA AGT     1018
Glu Asn His Ser Arg Ile Leu Pro Glu Asn Phe Gly Ser Val Arg Ser
                310                 315                 320

CAG CTC TCT TCA TCC AGT AAG TTC ATA CCA GGG GTC CCC ACT TGC TTT     1066
Gln Leu Ser Ser Ser Lys Phe Ile Pro Gly Val Pro Thr Cys Phe
            325                 330                 335

GAA ATA AAA CCT GAA GAA AAT TCA GAT GTT CAT GAA TTG AGA GTA AAA     1114
Glu Ile Lys Pro Glu Glu Asn Ser Asp Val His Glu Leu Arg Val Lys
                340                 345                 350

CGT TCT GTT ACA AGA ATA AAA AAG AGA TCT CGA AGT GTT TTC TAC AGG     1162
Arg Ser Val Thr Arg Ile Lys Lys Arg Ser Arg Ser Val Phe Tyr Arg
        355                 360                 365

CTG ACC ATA CTG ATA TTA GTA TTT GCT GTT AGT TGG ATG CCA CTA CAC     1210
Leu Thr Ile Leu Ile Leu Val Phe Ala Val Ser Trp Met Pro Leu His
370             375                 380                 385

CTT TTC CAT GTG GTA ACT GAT TTT AAT GAC AAT CTT ATT TCA AAT AGG     1258
Leu Phe His Val Val Thr Asp Phe Asn Asp Asn Leu Ile Ser Asn Arg
                390                 395                 400

CAT TTC AAG TTG GTG TAT TGC ATT TGT CAT TTG TTG GGC ATG ATG TCC     1306
His Phe Lys Leu Val Tyr Cys Ile Cys His Leu Leu Gly Met Met Ser
        405                 410                 415

TGT TGT CTT AAT CCA ATT CTG TAT GGA TTT CTT AAT AAT GGG ATT AAA     1354
Cys Cys Leu Asn Pro Ile Leu Tyr Gly Phe Leu Asn Asn Gly Ile Lys
            420                 425                 430

GCT GAT TTA ATG TCC CTT ATA CAC TGT CTT CAT ATG TAATAATTCT         1400
Ala Asp Leu Met Ser Leu Ile His Cys Leu His Met
435                 440                 445

CAGACTAGTC AAGCCGAATT CCAGCACACT GGCGGCCGTT AC                     1442
```

(2) INFORMATION FOR SEQ ID NO: 4:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO: 4:

-continued

```
Met Asp Leu Glu Leu Asp Glu Tyr Tyr Asn Lys Thr Leu Ala Thr Glu
 1               5                  10                  15

Asn Asn Thr Ala Ala Thr Arg Asn Ser Asp Phe Pro Val Trp Asp Asp
                20                  25                  30

Tyr Lys Ser Ser Val Asp Asp Leu Gln Tyr Phe Leu Ile Gly Leu Tyr
            35                  40                  45

Thr Phe Val Ser Leu Leu Gly Phe Met Gly Asn Leu Leu Ile Leu Met
        50                  55                  60

Ala Leu Met Lys Lys Arg Asn Gln Lys Thr Thr Val Asn Phe Leu Ile
 65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Val
               100                 105                 110

Met Cys His Ile Met Pro Phe Leu Gln Cys Val Ser Val Leu Val Ser
            115                 120                 125

Thr Leu Ile Leu Ile Ser Ile Ala Ile Val Arg Tyr His Met Ile Lys
        130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
            180                 185                 190

Ser Ser Arg Tyr Leu Cys Val Glu Ser Trp Pro Ser Asp Ser Tyr Arg
        195                 200                 205

Ile Ala Phe Thr Ile Ser Leu Leu Val Gln Tyr Ile Leu Pro Leu
210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Arg Lys Ile Gly Pro Gln Val Lys Leu Ser
            260                 265                 270

Gly Ser His Lys Trp Ser Tyr Ser Phe Ile Lys Lys His Arg Arg Arg
        275                 280                 285

Tyr Ser Lys Lys Thr Ala Cys Val Leu Pro Ala Pro Glu Arg Pro Ser
290                 295                 300

Gln Glu Asn His Ser Arg Ile Leu Pro Glu Asn Phe Gly Ser Val Arg
305                 310                 315                 320

Ser Gln Leu Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365

Arg Leu Thr Ile Leu Ile Leu Val Phe Ala Val Ser Trp Met Pro Leu
370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
```

-continued

```
                420              425              430
Lys Ala Asp Leu Met Ser Leu Ile His Cys Leu His Met
            435              440              445
```

(2) INFORMATION FOR SEQ ID NO: 5:

(i) SEQUENCE CHARACTERISTICS:
        (A) LENGTH: 1442 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 5:

```
CUCGAGCGGC CGCCAGUGUG AUGGAUAUCU GCAGAAUUCG GCUUAGGACU AUAAUAUGGA    60
UUUAGAGCUC GAUGAAUAUU AUAACAAGAC ACUUGCCACA GAGAAUAAUA CUGCUGCCAC   120
UCGGAAUUCU GAUUUCCCAG UCUGGGAUGA CUAUAAAAGC AGUGUAGAUG ACUUACAGUA   180
UUUUCUGAUU GGGCUCUAUA CAUUUGUAAG UCUUCUUGGC UUUAUGGGGA AUUUACUUAU   240
UUUAAUGGCU CUCAUGAAAA AGCGUAAUCA GAAGACUACG GUAAACUUCC UUAUAGGAAA   300
UCUGGCCUUU UCUGAUAUCU UGGUUGUGCU GUUUUGCUCA CCUUUCACAC UGACAUCUGU   360
CUUGCUGGAU CAGUGGAUGU UUGGCAAAGU CAUGUGCCAU AUUAUGCCUU UUCUGCAAUG   420
CGUGUCAGUU UUGGUUUCAA CUUUAAUUUU AAUAUCAAUU GCCAUUGUCA GGUAUCAUAU   480
GAUAAAACAU CCCAUCUCUA AUAAUUUAAC AGCAAACCAU GGCUACUUUC UGAUAGCUAC   540
UGUCUGGACA CUAGGUUUUG CCAUCUGUUC UCCCCUUCCA GUGUUUCACA GUCUUGUGGA   600
ACUUCAAGAA ACAUUUGGUU CAGCGUUGCU GAGCAGCAGG UAUUUAUGUG UUGAGUCAUG   660
GCCAUCUGAU UCAUACAGAA UUGCCUUUAC UAUCUCUUUA UUGCUAGUUC AGUAUAUUCU   720
GCCCUUAGUU UGUCUUACUG UAAGUCAUAC AAGUGUCUGC AGAAGCAUAA GCUGUGGAUU   780
GUCCAACAAA GAAAACAGAC UUGAAGAAAA UGAGAUGAUC AACUUAACUC UUCAUCCAUC   840
CAGAAAGAUU GGGCCUCAGG UGAAACUCUC UGGCAGCCAU AAAUGGAGUU AUUCAUUCAU   900
CAAAAAACAC AGAAGGAGAU AUAGCAAGAA GACAGCAUGU GUGUUACCCG CUCCAGAAAG   960
ACCUUCUCAA GAGAACCACU CCAGAAUACU UCCAGAAAAC UUUGGCUCUG UAAGAAGUCA  1020
GCUCUCUUCA UCCAGUAAGU UCAUACCAGG GGUCCCACU UGCUUUGAAA UAAAACCUGA  1080
AGAAAAUUCA GAUGUUCAUG AAUUGAGAGU AAAACGUUCU GUUACAAGAA UAAAAAAGAG  1140
AUCUCGAAGU GUUUUCUACA GGCUGACCAU ACUGAUAUUA GUAUUUGCUG UUAGUUGGAU  1200
GCCACUACAC CUUUUCCAUG UGGUAACUGA UUUUAAUGAC AAUCUUAUUU CAAAUAGGCA  1260
UUUCAAGUUG GUGUAUUGCA UUUGUCAUUU GUUGGGCAUG AUGUCCUGUU GUCUUAAUCC  1320
AAUUCUGUAU GGAUUUCUUA AUAAUGGGAU UAAAGCUGAU UUAAUGUCCC UUAUACACUG  1380
UCUUCAUAUG UAAUAAUUCU CAGACUAGUC AAGCCGAAUU CCAGCACACU GGCGGCCGUU  1440
AC                                                                1442
```